(12) United States Patent
Hibino et al.

(10) Patent No.: US 8,563,790 B2
(45) Date of Patent: Oct. 22, 2013

(54) PROCESS FOR PRODUCTION OF 2-CHLORO-3,3,3-TRIFLUOROPROPENE

(75) Inventors: Yasuo Hibino, Shiki (JP); Fumihiro Kawagoe, Kawagoe (JP); Fuyuhiko Sakyu, Iruma-gun (JP)

(73) Assignee: Central Glass Company, Limited, Ube-shi (JP)

( * ) Notice: Subject to any disclaimer, the term of this patent is extended or adjusted under 35 U.S.C. 154(b) by 0 days.

(21) Appl. No.: 13/383,708

(22) PCT Filed: Jul. 16, 2010

(86) PCT No.: PCT/JP2010/062034
§ 371 (c)(1),
(2), (4) Date: Jan. 12, 2012

(87) PCT Pub. No.: WO2011/010606
PCT Pub. Date: Jan. 27, 2011

(65) Prior Publication Data
US 2012/0123173 A1     May 17, 2012

(30) Foreign Application Priority Data

Jul. 21, 2009  (JP) ................................ 2009-170597
Jul. 8, 2010   (JP) ................................ 2010-155313

(51) Int. Cl.
*C07C 19/08*  (2006.01)

(52) U.S. Cl.
USPC ........................................................ 570/176

(58) Field of Classification Search
None
See application file for complete search history.

(56) References Cited

U.S. PATENT DOCUMENTS

| 5,097,082 A |  | 3/1992 | Anton |
| 5,118,888 A |  | 6/1992 | Gervasutti et al. |
| 6,459,008 B1 | * | 10/2002 | Dai et al. ..................... 585/651 |
| 6,958,424 B1 |  | 10/2005 | Nair et al. |

| 2007/0197842 A1 | 8/2007 | Mukhopadhyay et al. |
| 2009/0030244 A1 | 1/2009 | Merkel et al. |
| 2009/0124837 A1 | 5/2009 | Mukhopadhyay et al. |

FOREIGN PATENT DOCUMENTS

| EP | 0 053 657 A1 | 6/1982 |
| EP | 0 396 974 A1 | 11/1990 |
| JP | 57-122021 A | 7/1982 |
| JP | 62-30730 A | 2/1987 |
| JP | 62-207233 A | 9/1987 |
| JP | 2-286635 A | 11/1990 |
| JP | 2009-137945 A | 6/2009 |
| WO | WO 91/18854 A1 | 12/1991 |
| WO | WO 2007/079431 A2 | 7/2007 |
| WO | WO 2008030440 A2 * | 3/2008 |

OTHER PUBLICATIONS

PCT/ISA/237 Form (Three (3) pages).
International Search Report including English language translation dated Sep. 7, 2010 (Five (5) pages).
R. N. Haszeldine, "Reactions of Fluorocarbon Radicals. Part V. Alternative Syntheses for Trifluoromethylacetylene (3 : 3 : 3-Trifluoropropyne), and the Influence of Polyfluoro-groups on Adjacent Hydrogen and Halogen Atoms", J. Chem. Soc., 1951, pp. 2495-2504.

* cited by examiner

*Primary Examiner* — Johann R Richter
*Assistant Examiner* — Medhanit Bahta
(74) *Attorney, Agent, or Firm* — Crowell & Moring LLP

(57) ABSTRACT

There is provided according the present invention a process for producing 2-chloro-3,3,3-trifluoropropene, comprising: hydrogenating 1,2-dichloro-3,3,3-trifluoropropene with hydrogen ($H_2$) in the presence of a catalyst having a transition metal and a poisoning substance supported on a support. The present production process is industrially advantageous as the target 2-chloro-3,3,3-trifluoropropene can be obtained with high selectivity and high yield under moderate reaction conditions and with easy waste treatment.

9 Claims, No Drawings

PROCESS FOR PRODUCTION OF 2-CHLORO-3,3,3-TRIFLUOROPROPENE

TECHNICAL FIELD

The present invention relates to a process for production of 2-chloro-3,3,3-trifluoropropene.

BACKGROUND ART

A large number of researches have been made on the uses of 2-chloro-3,3,3-trifluoropropene and derivatives of 2-chloro-3,3,3-trifluoropropene as this compound has a trifluoromethyl ($CF_3$) group and a double bond in its molecule and exhibits specific features. For example, Japanese Laid-Open Patent Publication No. 2009-137945 discloses a process for producing 2,3,3,3-tetrafluoropropene, which is usable as a coolant or a blowing agent, with the use of 2-chloro-3,3,3-trifluoropropene.

As methods for production of 2-chloro-3,3,3-trifluoropropene, Patent Document 1 discloses a process in which 1-chloro-1,1-dihalotrifluoroethane is reacted with an aldehyde compound in the presence of an electrophilic reagent and a zinc powder; and Patent Document 2 discloses a process in which a chlorinated propane such as 1,1,2,3-tetrachloropropene is reacted with hydrogen fluoride. Further, Non-Patent Document 1 discloses a process for producing 2-chloro-3,3,3-trifluoropropene by dehydrochlorination reaction of 1,2-dichloro-3,3,3-trifluoropropane with potassium hydroxide.

Patent Document 3 discloses a process for producing 1-chloro-3,3,3-trifluoropropene and 3,3,3-trifluoropropene by reduction of 1,2-dichloro-3,3,3-trifluoropepene, which is a starting material of the present invention, with a formate in a liquid phase in the presence of a palladium catalyst. This process generally gives 1-chloro-3,3,3-trifluoropropene and 3,3,3-trifluoropropene at a ratio of 4:6 but does not give 2-chloro-3,3,3-trifluoropropene, which is the target compound of the present invention.

PRIOR ART DOCUMENTS

Patent Documents

Patent Document 1: Japanese Laid-Open Patent Publication No. S62-207233
Patent Document 2: U.S. Patent Application Publication No. 2009/0030244
Patent Document 3: U.S. Pat. No. 6,958,424

Non-Patent Documents

Non-Patent Document 1: R. N. Haszeldine et al., J. Chem. Soc., 1951, P.2495-2504

SUMMARY OF THE INVENTION

Problems to be Solved by the Invention

Although the chlorofluorocarbon (CFC) or bromochlorofluorocarbon is used as the starting material in the process of Patent Document 1, it is currently undesirable to use the chlorofluorocarbon or bromochlorofluorocarbon due to the fact that the use of the chlorofluorocarbon or bromochlorofluorocarbon could lead to destruction of the ozone layer. In addition, there is a need for a complicated operation to extract the target compound from the catalyst-containing reaction product so that it is difficult to adopt the process of Patent Document 1 in view of the efficiency of the process operation as the reaction proceeds catalytically in an aprotic solvent in the process of Patent Document 1. It is difficult to adopt the process of Patent Document 2 due to the fact that the reaction temperature is very high (up to 350° C.) and that the selectivity of 2-chloro-3,3,3-trifluoropropene, which is the target compound of the present invention, is very low. In the process of Non-Patent Document 1, the selectivity of the reaction is so low that it is very difficult to obtain the target compound with high yield. Further, the production route using 1,2-dichloro-3,3,3-trifluoropropane as the starting material proceeds in a plurality of stages. It is thus difficult to adopt the process of Non-Patent Document 1 as an industrial production method.

As mentioned above, the conventional processes are not always satisfactory as industrial methods for mass production of 2-chloro-3,3,3-trifluoropropene, that is, the target compound of the present invention. There has been a demand to establish an easily practicable process for industrial-scale production of the target compound of the present invention.

It is therefore an object of the present invention to provide an industrial production process suitable for mass production of 2-chloro-3,3,3-trifluoropropene.

Means for Solving the Problems

The present inventors have made extensive researches to solve the above problems and, as a result, have found that it is possible to obtain 2-chloro-3,3,3-trifluoropropene of the formula [2] with high selectivity and high yield by hydrogenating 1,2-dichloro-3,3,3-trifluoropropene of the formula [1] with hydrogen ($H_2$) in the presence of a catalyst having a transition metal and a poisoning substance supported on a support.

[Chem. 1]

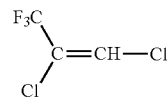

[1]

[Chem. 2]

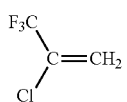

[2]

Namely, the present invention provides a process for production of 2-chloro-3,3,3-trifluoropropene as defined in the following Inventive Aspects [1] to [5].

[1] A process for producing 2-chloro-3,3,3-trifluoropropene of the formula [2], comprising: hydrogenating 1,2-dichloro-3,3,3-trifluoropropene of the formula [1] with hydrogen ($H_2$) in the presence of a catalyst having a transition metal and a poisoning substance supported on a support.

[2] The process according to Inventive Aspect 1, wherein the catalyst is either a palladium-bismuth/activated carbon catalyst, a palladium-lead/activated carbon catalyst, a palladium-bismuth-lead/activated carbon catalyst or a palladium-bismuth/alumina catalyst.

[3] The process according to Inventive Aspect 1 or 2, wherein the amount of the catalyst used is 0.05 to 10 mass % per 1 mole of 1,2-dichloro-3,3,3-trifluoropropene of the formula [1].

[4] The process according to any one of Inventive Aspects 1 to 3, wherein the poisoning substance is either a nitrate, a chloride or an oxide of at least one kind of metal selected from the group consisting of metals of Groups 2 to 5 and Groups 11 to 15 of the periodic table.

[5] The process according to any one of Inventive Aspects 1 to 3, wherein the mole ratio of the transition metal and the poisoning substance is 100/1 to 1/10 in terms of metal content.

Although there are a plurality of documents reporting on the hydrogenation reduction (reductive dehalogenation) of halogenated olefins, it is very difficult to find reaction conditions for selectively converting a halogen atom of a compound in which a plurality of halogen atoms are bonded to an olefin moiety (double-bond moiety) to a hydrogen atom. The reduction reaction often leads to an unexpected result especially in the case where a strong electron-withdrawing group, i.e., trifluoromethyl group is bonded to the olefin moiety. For these reasons, it has been unknown whether the hydrogenation of 1,2,-dichloro-3,3,3-trifluoropropene with hydrogen would enable selective conversion of a chlorine atom bonded to the 1-position carbon atom to a hydrogen atom to produce 2-chloro-3,3,3-trifluoropropene with high selectivity and high yield.

[Chem. 3]

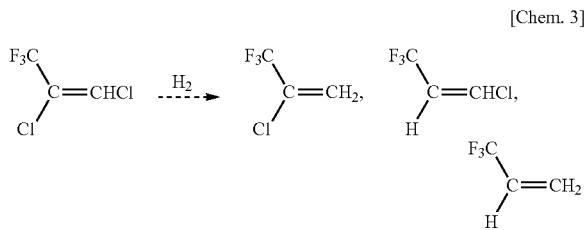

However, the present inventors have found a simple and practically advantageous industrial-scale production method by which it is possible to obtain 2-chloro-3,3,3-trifluoropropene with high selectivity and high yield even under industrially easily practicable production conditions by hydrogenation of 1,2-dichloro-3,3,3-trifluoropropene in the presence of a catalyst having a transition metal and a poisoning substance supported on a support (see the after-mentioned Examples).

The target compound of the present invention, that is, 2-chloro-3,3,3-trifluoropropene has a low boiling point of 14 to 15° C. and thus exist in gaseous form under ambient temperature and atmospheric pressure (0.1 MPa) conditions. It is thus feasible to obtain the target compound by allowing a crude product gas, generated in a flow gas phase reactor or pressure-resistant reaction vessel and containing 2-chloro-3,3,3-trifluoropropene, to pass through a condenser, while cooling the condenser at a temperature lower than 0° C. and, more specifically, lower than the boiling point of the target compound, thereby removing excessive hydrogen gas etc. from the crude product gas and condensing the product gas. The crude product can be purified by, after washing a trace amount of acid etc. away with water, distillation separation operation.

It is therefore possible according to the present invention to produce the target 2-chloro-3,3,3-trifluoropropene with higher yield than that of conventional process, with no environmental load and with high productivity under industrially easily practicable production conditions.

BEST MODES FOR CARRYING OUT THE INVENTION

Hereinafter, the present invention will be described in detail below.

The present invention refers to a production process of 2-chloro-3,3,3-trifluoropropene of the formula [2], including hydrogenating 1,2-dichloro-3,3,3-trifluoropropene of the formula [1] with hydrogen ($H_2$) in the presence of a catalyst having a transition metal and a poisoning substance supported on a support (hereinafter occasionally just referred to as "supported metal catalyst"). In the supported metal catalyst, the transition metal is in a different group of the periodic table from a metal of the poisoning substance as will be explained in detail later.

There is no particular limitation on the reaction system and reactor in the present production process. The reaction system and reactor can be of continuous type, semi-continuous type or batch type as selected as appropriate by those skilled in the art.

There is also no particular limitation 1,2-dichloro-3,3,3-trifluoropropene of the formula [1] used as the starting material in the present production process. For example, it is feasible to obtain 1,2-dichloro-3,3,3-trifluoropropene by reaction of 1,2,2-trichloro-3,3,3-trifluoropropane with potassium hydroxide as disclosed in Non-Patent Publication 1. Further, 1,2-dichloro-3,3,3-trifluoropropene can be easily obtained by chlorination of 1-chloro-3,3,3-trifluoropropene in a gas phase in the presence of an activated carbon, an antimony/activated carbon catalyst etc. Although there exist trans (E) and cis (Z) isomers of 1,2-dichloro-3,3,3-trifluoropropene, there is no particular limitation on the isomer form of 1,2-dichloro-3,3,3-trifluoropropene used in the present production process. The trans and cis isomers can be used solely or in the form of a mixture thereof.

Examples of the transition metal of the supported metal catalyst are nickel (Ni), platinum (Pt), iridium (Ir), rhodium (Rh), cobalt (Co), iron (Fe), ruthenium (Ru), palladium (Pd), chromium (Cr) and rhenium (Re). Among these transition metals, preferred are transition metals of Group 8, Group 9 and Group 10 of the periodic table. More specifically, nickel, palladium, platinum, rhodium, ruthenium and iridium are preferred.

Examples of the support of the supported metal catalyst are alumina, fluorinated alumina, aluminum fluoride, activated carbon, zirconia, calcium carbonate, calcium fluoride, barium carbonate and silica.

Specific examples of the activated carbon usable as the support are plant-based activated carbons prepared using wood, wood charcoal, coconut shell charcoal, palm shell charcoal, raw ash etc. as raw materials; coal-based activated carbons prepared using peat coal, lignite, brown coal, bituminous coal, anthracite etc. as raw materials; petroleum-based activated carbons prepared using petroleum pitch, oil carbon etc. as raw materials; and synthetic resin-based activated carbons prepared using polyvinylidene chloride etc. as raw materials. These activated carbons are commercially available and usable. For example, there can be used coconut shell activated carbon (available under the trade name of Granular Shirasagi GX, G2X, SX, CX or XRC from Japan EnviroChemicals Ltd. or available under the trade name of PCB from Mitsubishi Chemical Calgon Co., Ltd.). The activated carbon is not however limited to the above examples. In general, the activated carbon is used in the form of particles. The shape and size of the activated carbon can be selected as appropriate based on the general knowledge of those skilled in the art as long as the activated carbon is adaptable to the reactor. The activated carbon can be in various forms such as spherical form, fibrous form, powder form and honeycomb form. Preferably, the activated carbon used has a large specific surface in the present production process. The specific surface and pore volume of the activated carbon can be within the specifications of commercially available activated carbons. It is particularly preferable that the activated carbon has a specific surface of larger than 400 m²/g and a pore volume of larger than 0.1 cm³/g, more preferably a specific surface of 800 to 3000 m²/g and a pore volume of 0.2 to 1.0 cm³/g. It is further preferable, in the case of using the activated carbon as the support, to activate a surface of the support and remove an ash content from the support by pretreatment of the support with an acid such as nitric acid, hydrochloric acid or hydrofluoric acid as is commonly done.

In the present production process, the target 2-chloro-3,3,3-trifluoropropene of the formula [2] can be produced with higher selectivity due to the coexistence of a metal that is in a different group of the periodic table from the above-mentioned transition metal as the poisoning substance in the reaction system. In the case of using a transition metal having a high reduction power, such as palladium, chlorine atoms bonded to 1- and 2-position carbon atoms of the 1,2-dichloro-3,3,3-trifluoropropene are reduced nonselectively. In order keep the chlorine atom bonded to the 2-position carbon atom and thereby obtain the target 2-chloro-3,3,3-trifluoropropene efficiently, it is preferable to lower the reaction temperature, weaken the reaction conditions and/or poison the catalyst with the poisoning substance.

As such a poisoning substance, there can be used at least one kind of metal selected from the group consisting of metals of Group 2, Group 3, Group 4, Group 5, Group 11, Group 12, Group 13, Group 14 and Group 15 of the periodic table. Examples of the metal used as the poisoning substance are bismuth (Bi), zinc (Zn), copper (Cu), silver (Ag), lanthanum (La), lead (Pb), zirconium (Zr), niobium (Nb), hafnium (Hf), magnesium (Mg), tin (Sn), arsenic (As) and thallium (Tl). Among others, bismuth and lead are preferred for industrial use. The poisoning substance is preferably in the form of a nitrate, a chloride or an oxide of the above metal, which is soluble in a solvent such as water, ethanol or acetone. As mentioned above, the metal used as the poisoning substance is preferably different from the transition metal used for preparation of the supported metal catalyst. Further, the above metals can be used solely or in combination of two or more thereof as the poisoning substance.

Specific examples of the supported metal catalyst usable in the present production process are a palladium-bismuth/activated carbon catalyst (Pd—Bi/C), a palladium-bismuth/alumina catalyst (Pd—Bi/Al₂O₃), a palladium-bismuth/zirconia catalyst (Pd—Bi/ZrO₂), a palladium-lead/activated carbon catalyst (Pd—Pb/C), a palladium-lead/alumina catalyst (Pd—Pb/Al₂O₃), a palladium-lead/zirconia catalyst (Pd—Pb/ZrO₂), a palladium-bismuth-lead/activated carbon catalyst (Pd—Bi—Pb/C) and a palladium-bismuth-lead/alumina catalyst (Pd—Bi—Pb/Al₂O₃). Among others, a palladium-bismuth/activated carbon catalyst, a palladium-bismuth/alumina catalyst, a palladium-lead/activated carbon catalyst and a palladium-bismuth-lead/activated carbon catalyst are preferred. Particularly preferred is a palladium-bismuth/activated carbon catalyst.

There is no particular limitation on the process for preparation of the supported metal catalyst. The process for preparation of the supported metal catalyst can be selected as appropriate by those skilled in the art. The amount of the transition metal supported is generally 0.01 to 80 mass %, preferably 0.2 to 40 mass %, based on the amount of the support.

It is preferable to support both of the transition metal and the metal of the poisoning substance in the form of soluble compounds on the support. Examples of such soluble metal compounds are nitrates, chlorides, oxychlorides and oxides of the metals, each of which is soluble in a solvent such as water, methanol, ethanol or acetone.

The mole ratio of the transition metal and the poisoning substance is 100/1 to 1/10, preferably 10/1 to 1/2, in terms of metal content.

In the case of batch reaction system, it suffices to use a catalytic amount of the supported metal catalyst. The amount of the supported metal catalyst used is generally preferably 0.05 to 10 mass %, more preferably 0.5 to 5 mass %, per 1 mol of 1,2-dichloro-3,3,3-trifluoropropene of the formula [1].

Further, it suffices to use the hydrogen (H₂) in a stoichiometrically equivalent amount or more, i.e., in an amount of 1 mol or more, per 1 mol of 1,2-dichloro-3,3,3-trifluoropropene of the formula [1]. The amount of the hydrogen used is preferably 2 to 30 mol per 1 mol of 1,2-dichloro-3,3,3-trifluoropropene of the formula [1]. The pressure of the hydrogen can be set to be higher than or equal to atmospheric pressure in the case of flow reaction system. In order to perform the desired reaction efficiently, it is preferable to set the hydrogen pressure to 0.1 to 5.0 MPa (relative to the absolute pressure, the same applies to the following). The hydrogen pressure is particularly preferably set to 0.1 to 2.0 MPa in view of practicality. In the case of batch reaction system, the pressure of the hydrogen is preferably set higher than atmospheric pressure, more preferably 0.2 to 10 MPa. The hydrogen pressure is particularly preferably set to 0.5 to 5.0 MPa in view of practicality. Further, it is preferable that a base such as sodium hydroxide coexists as an acid accepter as there occurs hydrogen chloride in the batch reaction system.

In the case of flow reaction system, the contact time is generally in the range of 0.1 to 300 seconds, preferably 1 to 60 seconds. In the case of batch reaction system, the reaction time is no particularly limited and is generally 72 hours or fewer. As the reaction time varies depending on the catalyst, raw material substrate and reaction conditions, it is preferable to determine the time at which the raw material substrate has almost disappeared as the end of the reaction while monitoring the progress of the reaction by any analytical means such as gas chromatography, thin layer chromatography, liquid chromatography or nuclear magnetic resonance.

In the present production process, a solvent can be added into the reaction system. There is no particular limitation on the solvent as long as the solvent is not involved in the reaction. Examples of the solvent are: water; aliphatic hydrocarbons such as n-hexane, cyclohexane and n-heptane; aromatic hydrocarbons such as benzene, toluene, α,α,α-trifluorotoluene, xylene, ethylbenzene and mesitylene; halogenated hydrocarbons such as methylene chloride, chloroform and 1,2-dichloroethane; and ethers such as diethyl ether, 1,2-dimethoxyethane, 1,4-dioxane, tetrahydrofuran, 2-methyltetrahydrofuran, tert-butyl methyl ether, diisopropyl ether, diethylene glycol monoethyl ether and anisole. Among others, n-hexane, n-heptane, toluene, xylene, diethyl ether, 1,4-dioxane and tetrahydrofuran are preferred. Particularly preferred are n-hexane, toluene, diethyl ether and tetrahydrofuran. These solvents can be used solely or in combination of two or more thereof.

There is no particular limitation on the reaction pressure in the present production process. The reaction can be performed under normal pressure conditions or pressurized conditions. The reaction pressure is generally in the range of 0.1 to 2 MPa, preferably 0.1 to 0.5 MPa.

When the reaction is performed under pressurized conditions, there is no particular limitation on the material of the reactor as long as the reactor is capable of withstanding such pressurized conditions. As the reactor, there can be used a reaction vessel with a lining of tetrafluoroethylene resin, chlorotrifluoroethylene resin, vinylidene fluoride resin, PFA resin, glass or the like or a reaction vessel of glass. Although the reaction itself proceeds in a reaction vessel with a metal lining of stainless steel, iron or the like, the metal lining could be subjected to corrosion by hydrogen chloride gas generated during the progress of the reaction in the present production process. It is thus preferable to use the above-mentioned reaction vessel.

There is also no particular limitation on the reaction temperature. The reaction temperature is generally in the range of 100 to 600° C., preferably 120 to 350° C. If the reaction temperature is lower than 100° C., the reaction becomes too slow to be practical. If the reaction temperature exceeds 600° C., the life of the catalyst becomes shortened. In addition, the reaction proceeds fast but causes a decomposition product so that the selectivity of the target 2-chloro-3,3,3-trifluoropropene may be lowered.

In the present production process, an over-reduced compound such as 3,3,3-trifluoropropene or 1,1,1-trifluoropropane and a trace amount of 1-chloro-3,3,3-trifluoropropene may be generated as by-products in addition to the target 2-chloro-3,3,3-trifluoropropene. It is feasible to convert these by-products to 1,2-dichloro-3,3,3-trifluoropropane or 1,2-dichloro-3,3,3-trifluoropropene and then to 2-chloro-3,3,3-trifluoropropene by chlorination in a gas phase in the presence of an activated carbon, an antimony/activated carbon catalyst or the like. Further, 3,3,3-trifluoropropene may be generated by hydrogenation of 1-chloro-3,3,3-trifluoropropene, which is a precursor of 1,2-dichloro-3,3,3-trifluoropropene, in the presence of a gas-phase reduction catalyst and can be converted to 2-chloro-3,3,3-trifluoropropene. It is feasible to convert 3,3,3-trifluoropropene to 2-chloro-3,3,3-trifluoropropene by gas phase chlorination in the same manner as above. The impurity components such as hydrogenation by-product can be recovered by separation, returned to the reactor and reused.

Herein, the 2-chloro-3,3,3-trifluoropropene (boiling point: 15° C.) obtained in the present production process exists as a gas under ambient temperature and atmospheric pressure (0.1 MPa) conditions. It is thus feasible to obtain the target 2-chloro-3,3,3-trifluoropropene with high purity by allowing the obtained gas to pass through a condenser under cooling conditions so as to collect and liquefy the gas in a collector, subjecting the collected liquefied gas to deacidification by water washing, drying etc. as needed, and then, purifying the gas by precision distillation.

EXAMPLES

The present invention will be described in more detail below by way of the following examples. Herein, the unit "%" of each composition analysis value means the area percentage "area %" of an individual component as determined by gas chromatography of a reaction mixture. (Unless otherwise specified, a FID was used as a detector in gas chromatography.)

Preparation Example 1

Preparation of Palladium/Activated Carbon Catalyst

Into a 500-ml eggplant-shaped flask, 100 g of activated carbon (Granular Shirasagi G2X: 4/6-1 manufactured by Japan EnviroChemicals Ltd.) was weighed out accurately. The activated carbon was then subjected to nitric acid treatment by adding about 150 ml of an aqueous solution containing approximately 20% nitric acid to the activated carbon and leaving the mixture for about 3 hours. Further, a palladium (II) chloride hydrochloric acid solution was prepared by dissolving 0.834 g of palladium (II) chloride in 50 g of 24% hydrochloric acid. The prepared palladium chloride solution was dropped onto the nitric acid-treated activated carbon. The nitric acid-treated activated carbon was left still in the palladium chloride solution for 2 days. The thus-obtained metal-impregnated activated carbon was dried under reduced pressure by an evaporator and an oil bath. The temperature of the oil bath was gradually raised to 150° C. or higher to thereby remove water from the metal-impregnated activated carbon.

Preparation Example 2

Preparation of Palladium-Bismuth/Activated Carbon Catalyst

Into a 500-ml eggplant-shaped flask, 100 g of activated carbon (Granular Shirasagi G2X: 4/6-1 manufactured by Japan EnviroChemicals Ltd.) was weighed out accurately. The activated carbon was then subjected to nitric acid treatment by adding about 150 ml of an aqueous solution containing approximately 20% nitric acid to the activated carbon and leaving the mixture for about 3 hours. On the other hand, 0.696 g of bismuth (III) nitrate pentahydrate was mixed in 200 ml of an aqueous solution containing approximately 30% nitric acid in a 300-ml beaker, followed by heating the beaker in a hot water bath to completely dissolve the bismuth nitrate pentahydrate in the aqueous nitric acid solution. A palladium (II) chloride hydrochloric acid solution was prepared by dissolving 0.834 g of palladium (II) chloride in 50 g of 24% hydrochloric acid, and then, mixed with the above-prepared bismuth nitrate solution. The mixed solution was dropped onto the nitric acid-treated activated carbon. The nitric acid-treated activated carbon was left still in the mixed solution for 2 days. The thus-obtained metal-impregnated activated carbon was dried under reduced pressure by an evaporator and an oil bath. The temperature of the oil bath was gradually raised to 150° C. or higher to thereby remove water from the metal-impregnated activated carbon.

Preparation Example 3

Preparation of Palladium-Bismuth/Activated Carbon Catalyst

Into a 200-ml eggplant-shaped flask, 0.334 g of palladium (II) chloride was weighed out accurately. To the palladium chloride added was 1 g of 24% hydrochloric acid, thereby dissolving the palladium chloride in the hydrochloric acid. Separately, 0.278 g of bismuth (III) nitrate pentahydrate was weighed out and dissolved in 24 ml of 30% nitric acid. These two solutions were mixed together. Then, 20 g of activated carbon (Granular Shirasagi G2X: 4/6-1 manufactured by Japan EnviroChemicals Ltd.) was added to the mixed solution and left still in the mixed solution for 1 day. The thus-obtained metal-impregnated activated carbon was subjected to evaporation drying by an evaporator.

Preparation Example 4

Preparation of Palladium-Lead/Activated Carbon Catalyst

Into a 100-ml eggplant-shaped flask, 0.183 g of lead (II) acetate trihydrate was weighed out accurately. To the lead acetate trihydrate added was 30 ml of ion-exchanged water, thereby dissolving the lead acetate trihydrate in the ion-exchanged water. Then, 10 g of activated carbon (Granular Shirasagi G2X: 4/6-1 manufactured by Japan EnviroChemicals Ltd.) was added to the lead acetate trihydrate solution. The activated carbon was left still in the lead acetate trihydrate solution for about 1 day. The resulting metal-impregnated activated carbon was subjected to evaporation drying/hardening by an evaporator, followed by adding thereto 0.167 g of palladium (II) chloride and 30 ml of 8% hydrochloric acid and leaving the mixture still for 1 day. The thus-obtained metal-impregnated activated carbon was subjected to evaporation drying by an evaporator.

Preparation Example 5

Preparation of Palladium-Bismuth-Lead/Activated Carbon Catalyst

Into a 100-ml eggplant-shaped flask, 0.183 g of lead (II) acetate trihydrate was weighed out accurately. To the lead acetate trihydrate added was 30 ml of ion-exchanged water, thereby dissolving the lead acetate trihydrate in the ion-exchanged water. Then, 10 g of the palladium-bismuth/activated carbon catalyst prepared in Preparation Example 3 was added to and left in the lead acetate trihydrate solution for 1 day. The thus-obtained metal-impregnated activated carbon was subjected to evaporation drying by an evaporator.

Example 1

A reactor of SUS316L having an inside diameter of 20 A and a length of 30 cm was charged with 20 ml of the dried catalyst of Preparation Example 2. While flowing nitrogen through the reactor at a flow rate of 20 to 30 ml/min, the temperature of the reactor was raised by 50° C. from 150° C. to 300° C. The catalyst was then fired at 300° C. for about 1 hour. After that, the temperature of the reactor was lowered to 150° C. While flowing nitrogen at a flow rate of 10 ml/min and flowing hydrogen at a flow rate of 30 ml through the reactor, the temperature of the reactor was raised by 30° C. up to 300° C. Subsequently, the temperature of the reactor was lowered to 150° C. while flowing hydrogen through the reactor at a flow rate of 45 ml/min. In this state, 1,2-dichloro-3,3,3-trifluoropropene (Z isomer=90.5%, E isomer=9.5%) was introduced into the reactor at a flow rate of 15 ml/min. The reaction was stabilized after a lapse of about 2 hours. The thus-obtained product gas was sampled and analyzed by gas chromatography. As a result, the conversion rate of 1,2-dichloro-3,3,3-trifluoropropene was 99.0%; the selectivity of 2-chloro-3,3,3-trifluoropropene was 70.5%; and the (E/Z) selectivity of 1-chloro-3,3,3-trifluoropropene was 1.6%.

Example 2

A reactor of SUS316L having an inside diameter of 20 A and a length of 30 cm was charged with 10 ml of the dried catalyst of Preparation Example 1. While flowing nitrogen through the reactor at a flow rate of 20 to 30 ml/min, the temperature of the reactor was raised by 50° C. from 150° C. to 300° C. The catalyst was then fired at 300° C. for about 1 hour. After that, the temperature of the reactor was lowered to 150° C. While flowing nitrogen at a flow rate of 10 ml/min and flowing hydrogen at a flow rate of 30 ml through the reactor, the temperature of the reactor was raised by 30° C. up to 300° C. Subsequently, the temperature of the reactor was lowered to 150° C. while flowing hydrogen through the reactor at a flow rate of 45 ml/min. In this state, 1,2-dichloro-3,3,3-trifluoropropene (Z isomer=90.5%, E isomer=9.5%) was introduced into the reactor at a flow rate of 15 ml/min. The reaction was stabilized after a lapse of about 2 hours but was further continued. After a lapse of 5 hours, the thus-obtained product gas was sampled and analyzed by gas chromatography. As a result, the conversion rate of 1,2-dichloro-3,3,3-trifluoropropene was 34.3%; the selectivity of 2-chloro-3,3,3-trifluoropropene was 64.9%; and the (E/Z) selectivity of 1-chloro-3,3,3-trifluoropropene was 2.0%.

Example 3

The reaction was carried out using the same reactor under the same conditions as in Example 2, except that the reactor was charged with 10 ml of the dried catalyst of Preparation Example 4. The reaction was stabilized after a lapse of about 2 hours but was further continued. After a lapse of 5 hours, the thus-obtained product gas was sampled and analyzed by gas chromatography. As a result, the conversion rate of 1,2-dichloro-3,3,3-trifluoropropene was 84.9%; the selectivity of 2-chloro-3,3,3-trifluoropropene was 50.5%; and the (E/Z) selectivity of 1-chloro-3,3,3-trifluoropropene was 1.9%.

Example 4

The reaction was carried out using the same reactor under the same conditions as in Example 2, except that the reactor was charged with 10 ml of the dried catalyst of Preparation Example 5. The reaction was stabilized after a lapse of about 2 hours but was further continued. After a lapse of 5 hours, the thus-obtained product gas was sampled and analyzed by gas chromatography. As a result, the conversion rate of 1,2-dichloro-3,3,3-trifluoropropene was 80.1%; the selectivity of 2-chloro-3,3,3-trifluoropropene was 74.8%; and the (E/Z) selectivity of 1-chloro-3,3,3-trifluoropropene was 0.0%.

In this way, the target 2-chloro-3,3,3-trifluoropropene was obtained with much higher selectively and higher yield in each of Examples 1-4 where the reaction was performed in the presence of the catalyst having the transition metal and the poisoning substance supported on the support than in the following Comparative Examples 1-2.

Comparative Example 1

A reactor of SUS316L having an inside diameter of 20 A and a length of 30 cm was charged with 20 ml of the dried catalyst of Preparation Example 1. While flowing nitrogen through the reactor at a flow rate of 20 to 30 ml/min, the temperature of the reactor was raised by 50° C. from 150° C. to 300° C. The catalyst was then fired at 300° C. for about 1 hour. After that, the temperature of the reactor was lowered to 150° C. While flowing nitrogen at a flow rate of 10 ml/min and flowing hydrogen at a flow rate of 30 ml through the reactor, the temperature of the reactor was raised by 30° C. up to 300° C. Subsequently, the temperature of the reactor was lowered to 150° C. while flowing hydrogen through the reactor at a flow rate of 45 ml/min. In this state, 1,2-dichloro-3,3,3-trifluoropropene (Z isomer=90.5%, E isomer=9.5%) was introduced into the reactor at a flow rate of 15 ml/min. The reaction was stabilized after a lapse of about 2 hours. The thus-obtained product gas was sampled and analyzed by gas chromatography. As a result, the conversion rate of 1,2-dichloro-3,3,3-trifluoropropene was 99.9%; the selectivity of 3,3,3-trifluoropropene was 99.2%; and the selectivity of 2-chloro-3,3,3-trifluoropropene was 0.5%.

In Comparative Example 1 where the catalyst had only the transition metal supported on the support, almost no 2-chloro-3,3,3-trifluoropropene was obtained.

Comparative Example 2

A reactor of SUS316L having an inside diameter of 20 A and a length of 30 cm was charged with 20 ml of Re/activated carbon catalyst manufactured by N.E. Chemcat Corporation. While flowing nitrogen through the reactor at a flow rate of 20 to 30 ml/min, the temperature of the reactor was raised by 50° C. from 150° C. to 300° C. The catalyst was then fired at 300° C. for about 1 hour. After that, the temperature of the reactor was lowered to 150° C. While flowing nitrogen at a flow rate of 10 ml/min and flowing hydrogen at a flow rate of 30 ml through the reactor, the temperature of the reactor was raised by 30° C. up to 300° C. Subsequently, the temperature of the reactor was lowered to 150° C. while flowing hydrogen through the reactor at a flow rate of 45 ml/min. In this state, 1,2-dichloro-3,3,3-trifluoropropene (Z isomer=90.5%, E isomer=9.5%) was introduced into the reactor at a flow rate of 15 ml/min. After a lapse of about 1 hour, the thus-obtained product gas was sampled and analyzed by gas chromatography. The conversion rate of 1,2-dichloro-3,3,3-trifluoropropene was 90.0%; and the selectivity of 2-chloro-3,3,3-trifluoropropene was 60.0%. After a lapse of about 3 hours, the product gas was again sampled and analyzed by gas chromatography. As a result, the conversion rate of 1,2-dichloro-3,3,3-trifluoropropene was 99.0%; the selectivity of 1,2-dichloro-3,3,3-trifluoropropane was 93.9%; and the selectivity of 2-chloro-3,3,3-trifluoropropene was 0.7%.

As in the case of Comparative Example 1, almost no 2-chloro-3,3,3-trifluoropropene was obtained due to rapid deactivation of the catalyst in Comparative Example 2.

As described above, it is possible according to the present invention to produce the target 2-chloro-3,3,3-trifluoropropene with higher yield and productivity than that of conventional process and with no environmental load under industrially easily practicable production conditions. The 2-chloro-3,3,3-trifluoropropene obtained in the present production process is usable as a functional material e.g. a coolant, a blowing agent, a cleaning agent, a solvent, an etching agent or an aerosol, as an intermediate for a physiologically active agent or a functional material and as a monomer for a polymer.

Although the present invention has been described with reference to the above specific embodiments, the present invention is not limited to these exemplary embodiments. Various changes and modifications can be made to the above embodiments based on the ordinary knowledge of those skilled in the art without departing from the scope of the present invention.

The invention claimed is:

1. A process for producing 2-chloro-3,3,3-trifluoropropene of the formula [2], comprising: hydrogenating 1,2-dichloro-3,3,3-trifluoropropene of the formula [1] with hydrogen ($H_2$) in the presence of a catalyst

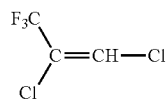

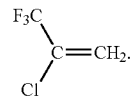

wherein the catalyst has a first and second metal supported on a catalyst support;
wherein the first metal is at least one metal selected from the group consisting of nickel (Ni), platinum (Pt), iridium (Ir), rhodium (Rh), cobalt (Co), iron (Fe), ruthenium (Ru), palladium (Pd), chromium (Cr) and rhenium (Re); and
wherein the second metal is at least one metal selected from the group consisting of bismuth (Bi), zinc (Zn), copper (Cu), silver (Ag), lanthanum (La), lead (Pb), zirconium (Zr), niobium (Nb), hafnium (Hf), magnesium (Mg), tin (Sn), arsenic (As) and thallium (Tl).

2. The process according to claim 1, wherein the first metal is at least one selected from the group consisting of nickel (Ni), platinum (Pt), iridium (Ir), rhodium (Rh), palladium (Pd) and rhenium (Re).

3. The process according to claim 1, wherein the second metal is at least one selected from the group consisting of bismuth (Bi) and lead (Pb).

4. The process according to claim 1, wherein the catalyst is at least one catalyst selected from the group consisting of a palladium-bismuth/activated carbon catalyst, a palladium-bismuth/alumina catalyst, a palladium-bismuth/zirconia catalyst, a palladium-lead/activated carbon catalyst, a palladium-lead/alumina catalyst, a palladium-lead/zirconia catalyst, a palladium-bismuth-lead/activated carbon catalyst and a palladium-bismuth-lead/alumina catalyst.

5. The process according to claim 4, wherein the catalyst is either a palladium-bismuth/activated carbon catalyst, a palladium-lead/activated carbon catalyst, a palladium-bismuth-lead/activated carbon catalyst or a palladium-bismuth/alumina catalyst.

6. The process according to claim 5, wherein the catalyst is a palladium-bismuth/activated carbon catalyst.

7. The process according to claim 1, wherein the second metal is supported in the form of either a nitrate, a chloride or an oxide thereof.

8. The process according to claim 1, wherein the amount of the catalyst used is 0.05 to 10 mass % per 1 mol of the 1,2-dichloro-3,3,3-trifluoropropene of the formula [1].

9. The process according to claim 1, wherein the mole ratio of the first metal and the second metal is in the range of 100/1 to 1/10 in terms of metal content.

* * * * *